(12) United States Patent
Bailey et al.

(10) Patent No.: US 10,524,740 B2
(45) Date of Patent: Jan. 7, 2020

(54) SELF-CONTAINED LOW COST CT SYSTEMS WITH INTEGRATED DRIVE SYSTEM

(71) Applicant: Dedicated2Imaging, LLC, Portsmouth, NH (US)

(72) Inventors: Eric M. Bailey, North Hampton, NH (US); Andrew Tybinkowski, Silver Lake, NH (US)

(73) Assignee: Dedicated2Imaging, LLC., Portsmouth, NH (US)

( * ) Notice: Subject to any disclaimer, the term of this patent is extended or adjusted under 35 U.S.C. 154(b) by 0 days.

(21) Appl. No.: 16/074,441

(22) PCT Filed: Apr. 11, 2017

(86) PCT No.: PCT/US2017/026919
§ 371 (c)(1),
(2) Date: Aug. 1, 2018

(87) PCT Pub. No.: WO2017/180568
PCT Pub. Date: Oct. 19, 2017

(65) Prior Publication Data
US 2019/0029612 A1    Jan. 31, 2019

Related U.S. Application Data

(60) Provisional application No. 62/320,623, filed on Apr. 11, 2016.

(51) Int. Cl.
*A61B 6/03*    (2006.01)
*A61B 6/04*    (2006.01)
*A61B 6/00*    (2006.01)

(52) U.S. Cl.
CPC ............ *A61B 6/035* (2013.01); *A61B 6/0407* (2013.01); *A61B 6/0457* (2013.01); *A61B 6/4411* (2013.01); *A61B 6/4435* (2013.01); *A61B 6/4447* (2013.01)

(58) Field of Classification Search
CPC ........... A61B 6/03; A61B 6/032; A61B 6/035; A61B 6/44; A61B 6/4429; A61B 6/4435; A61B 6/4447
See application file for complete search history.

(56) References Cited

U.S. PATENT DOCUMENTS 4,961,208 A * 10/1990 Okada ...................... A61B 6/04
                                                       250/363.04
5,042,487 A *  8/1991 Marquardt ........... A61B 6/0457
                                                       378/17

(Continued)

FOREIGN PATENT DOCUMENTS

WO    2008142695 A1    11/2008
WO    2013188617 A1    12/2013
WO    2016009316 A2     1/2016

*Primary Examiner* — Thomas R Artman (57) ABSTRACT

New and improved CT imaging systems are presented which are low cost, fully self-contained and easily installed/used. Example improvements include implementation of an integrated and self-contained drive system for moving a scanner component relative to a fixed or static platform/base which also acts as an imaging table. The CT imaging system is also greatly simplified to improve ease of use and to reduce cost.

30 Claims, 9 Drawing Sheets

(56) References Cited

U.S. PATENT DOCUMENTS

| | | | |
|---|---|---|---|
| 5,574,763 A * | 11/1996 | Dehner | A61B 6/032 378/17 |
| 6,735,274 B1 * | 5/2004 | Zahavi | A61B 6/032 378/15 |
| 6,776,527 B1 * | 8/2004 | Tybinkowski | A61B 6/04 378/195 |
| 7,224,764 B2 * | 5/2007 | Sukovic | A61B 6/032 378/19 |
| 7,388,941 B2 * | 6/2008 | Sukovic | A61B 6/032 378/19 |
| 7,394,888 B2 * | 7/2008 | Sukovic | A61B 6/032 378/20 |
| 8,118,488 B2 * | 2/2012 | Gregerson | A61B 5/0555 378/198 |
| 8,210,745 B2 * | 7/2012 | Yorkston | A61B 6/032 378/196 |
| 8,303,181 B2 * | 11/2012 | Sukovic | A61B 6/032 378/197 |
| 8,348,506 B2 * | 1/2013 | Yorkston | A61B 6/032 378/196 |
| 8,746,972 B2 * | 6/2014 | Yorkston | A61B 6/032 378/196 |
| 8,998,486 B2 * | 4/2015 | Yorkston | A61B 6/032 378/196 |
| 9,055,912 B2 * | 6/2015 | Graumann | A61B 6/4441 |
| 9,277,899 B2 * | 3/2016 | Yorkston | A61B 6/032 |
| 9,301,726 B2 * | 4/2016 | Mackie | A61B 6/4429 |
| 9,408,554 B2 * | 8/2016 | Gregerson | A61B 5/0555 |
| 9,597,044 B2 * | 3/2017 | Yorkston | A61B 6/032 |
| 9,687,200 B2 * | 6/2017 | Maurer, Jr. | A61B 6/032 |
| 9,700,272 B2 * | 7/2017 | Gregerson | A61B 5/0555 |
| 9,717,467 B2 * | 8/2017 | Litzenberger | A61B 6/548 |
| 9,770,214 B2 * | 9/2017 | Yorkston | A61B 6/032 |
| 9,833,208 B2 * | 12/2017 | Amano | A61B 6/037 |
| 9,907,516 B2 * | 3/2018 | Litzenberger | A61B 6/548 |
| 9,962,132 B2 * | 5/2018 | Gregerson | A61B 6/4447 |
| 10,010,295 B2 * | 7/2018 | Yorkston | A61B 6/032 |
| 10,034,641 B2 * | 7/2018 | Litzenberger | A61B 6/548 |
| 10,151,810 B2 * | 12/2018 | Gregerson | A61B 6/04 |
| 10,307,115 B2 * | 6/2019 | Yorkston | A61B 6/032 |
| 10,405,812 B2 * | 9/2019 | Litzenberger | A61B 6/025 |
| 10,413,265 B2 * | 9/2019 | Stoutenburgh | A61B 6/4035 |
| 2005/0053185 A1 * | 3/2005 | Sukovic | A61B 6/032 378/4 |
| 2005/0053186 A1 * | 3/2005 | Sukovic | A61B 6/032 378/4 |
| 2005/0054915 A1 * | 3/2005 | Sukovic | A61B 6/032 600/424 |
| 2006/0245539 A1 * | 11/2006 | Sukovic | A61B 6/032 378/20 |
| 2008/0205584 A1 * | 8/2008 | Sukovic | A61B 6/032 378/11 |
| 2010/0172468 A1 * | 7/2010 | Gregerson | A61B 5/0555 378/20 |
| 2011/0228910 A1 | 9/2011 | Gregerson et al. | |
| 2012/0324648 A1 * | 12/2012 | Amano | A61B 6/037 5/601 |
| 2012/0330087 A1 * | 12/2012 | Gregerson | A61B 5/0555 600/7 |
| 2014/0139215 A1 * | 5/2014 | Gregerson | A61B 6/04 324/309 |
| 2014/0265182 A1 | 9/2014 | Stanton et al. | |
| 2015/0208993 A1 | 7/2015 | Stoutenburgh et al. | |
| 2015/0313557 A1 * | 11/2015 | Mackie | A61B 6/04 378/14 |
| 2016/0338656 A1 * | 11/2016 | Gregerson | A61B 5/0555 |
| 2017/0071560 A1 * | 3/2017 | Gregerson | A61B 6/4447 |
| 2018/0125440 A1 * | 5/2018 | Gregerson | A61B 5/0555 |
| 2019/0029612 A1 * | 1/2019 | Bailey | A61B 6/035 |

* cited by examiner

SELF-CONTAINED LOW COST CT SYSTEMS WITH INTEGRATED DRIVE SYSTEM

CROSS-REFERENCE TO RELATED SECTIONS

The subject application claims the benefit of U.S. Provisional Application Ser. No. 62/320,623 filed Apr. 11, 2016 and entitled "Self-Contained Low Cost CT Systems with Integrated Drive System and Integrated Imaging Table" the contents of which are hereby incorporated herein in their entirety.

BACKGROUND

The subject application relates to computerized tomography (CT) imaging. In particular, new and improved CT imaging systems are presented which are low cost, fully self-contained and easily installed/used. Example improvements disclosed herein include implementation of an integrated and self-contained drive system for moving a scanner component relative to a fixed or static platform/base which also acts as an imaging table. The CT imaging system is also greatly simplified to improve ease of use and to reduce cost to a level similar to general X-ray and Ultrasound systems.

World population in 2016 is estimated to be in excess of seven billion people. However healthcare is not accessible to all. The "developed" world, consisting of mostly the USA, Western Europe, and Japan, enjoys the benefit of high tech medical devices which are not readily available in "less developed" regions of the world. Yet the developed world accounts for only 10% of the world population.

First and foremost among technologies not readily available in less developed regions of the world is the benefit of 3D diagnostic imaging technologies such as CT and MM. This is due to the reason for this is because of many barriers to initial ownership and operational costs. Whereas X-ray and Ultrasound systems retail for less than $150 k CT systems typically cost greater than $300 k and can exceed $1M. CT scanners are much more complex. They have a high failure rate and are more difficult to repair than X-ray and Ultrasound. Service contracts can typically exceed $100 k annually. In addition the repair personnel are designated as "service engineers", as opposed to "service technicians". These types of highly trained labor are scarce in underdeveloped nations.

Furthermore, the installation of a typical CT can take weeks in developed areas such as the USA. In underdeveloped countries this is much more difficult. Typical CT systems have to be anchored specifically to the Hospital floor, which has significant loading factors.

CT systems also require a tremendous amount of electrical power (40-120 kwatts) instantaneously when X-rays must energize. Significantly tight tolerances are required on the "cleanliness" of the power as to noise, spikes, dropouts, etc. In fact many CT systems are susceptible to poor quality power, which can cause long, complex, and costly service repairs to remediate each time. The power required is generally 3-phase 400/600volt, which requires special wiring, installation, and componentry such as transformers. This type of power is almost never available.

CT systems also typically occupy a very large footprint for the scanner portion because of the translating table. Generally rooms longer than 24 feet or greater than 7 meters are required. The room also requires fixed ventilation and radiation shielding. In addition another small room is required externally for the scan console. There may also be other storage requirements for items such as power modules. This room is rarely available in underdeveloped world and requires costly construction.

Furthermore, modern CT scanners are very complex pieces of equipment and thus require high intelligence and training to operate. But X-ray is a much easier technology to learn to use. As an analogy it is like comparing a Boeing 747 to a single engine Piper Cub aircraft. Highly trained CT technologists in the USA cost an institution approximately $100 k annually with benefits and overhead. In addition these scanners can be difficult to calibrate and certify as safe on a regular basis. This places a much higher burden on the hospital physics personnel, if there are such personnel in the first place.

Finally, today's CT scanners generally are versatile machines which may include various abilities, functionalities and extras that may represent a diminished return on investment. This is because a large hospital in the developed world will typically acquire a single ultra-expensive all-purpose machine covering a broad range of functionalities. This luxury packaging of features and versatility, however, may be unnecessary and cost prohibitive to many. Unfortunately, CT systems are not currently designed for limited cost at a trade-off of versatility.

Note that veterinary facilities have many of the same barriers listed above. With respect to CT and MRI technologies.

Thus, for at least the above noted reasons there exists a need for new and improved CT imaging systems which are low cost, fully self-contained and easily installed/used. These and other needs are met by way of the present disclosure.

SUMMARY

In example embodiments, a low-cost CT system is disclosed comprising a patient support table including a patient support surface extending between opposing support struts spaced apart from one another, a drive platform extending between the opposing support struts, and a scanner component defining a center opening configured for receiving a portion of a patient's anatomy, wherein the scanner component is movably mounted relative to the drive platform with the patient support surface passing through the center opening whereby the scanner component may be controllably translated along the drive platform so as to translate the scanner component relative to the patient support surface. Advantageously, the struts may include base portions thereof for mounting or anchoring the support table to a mounting surface e.g., wherein the drive platform extends between the base portions of the opposing support struts. In some embodiments, the patient support surface is a planar surface. Moreover, the support surface may be substantially horizontal and parallel to the ground. In further embodiments, the patient support surface may exhibit a high degree of radiolucency so as to not interfere with imaging. In some embodiments, the drive platform is a rail track. In further embodiments, the drive platform also forms a base of the table providing improved structural stability and mounting stability to the table. In example embodiments, the scanner component is less than 3 feet in length or approximately 2 feet in length. In further example embodiments, the drive platform is less than 10 feet in length or approximately 8 feet in length. In some embodiments the scanner component may be configured to exhibit a low rotational speed of less than 1 rotation per second or more preferably less than ½ a rotation per second. In further embodiments, the scanner component includes a fixed collimator. In some embodiments, different slice widths are achieved via a plurality of detector rows.

In example embodiments, the patient support surface of the table is laterally translatable relative to the struts of the table. Thus, e.g., a support surface drive platform may be included for enabling lateral translation of the patient support surface of the table. In some embodiments, the lateral translation of the patient support surface advantageously extends a scannable region thereof to a terminal end thereof. In example embodiments, the table may further include at least one hinged region of the patient support surface adapted for reconfiguring the patient support surface so as to reduce a footprint of the CT system. In yet further embodiments, an alignment platform may be included for adjusting a horizontal and/or vertical position of the scanner component relative to the drive platform and the table. In some embodiments, an alignment mechanism may be securable relative to the scanner component for facilitating alignment of an anatomical region of a patient.

In further example embodiments, a low-cost CT system is disclosed comprising a patient support table including a cantilevered patient support surface, a drive platform extending underneath the cantilevered patient support surface, and a scanner component defining a center opening configured for receiving a portion of a patient's anatomy, wherein the scanner component is movably mounted relative to the drive platform with the patient support surface passing through the center opening whereby the scanner component may be controllably translated along the drive platform so as to translate the scanner component relative to the patient support surface. In some embodiments, the table may include a truss support. In further embodiments, translation of the scanner component via the drive platform is not limited at the cantilevered end of the table thereby extending a scannable region of the cantilevered end to a terminus of the patient support surface.

In example embodiments, the scanner component may be advantageously shared between multiple tables. For example, in some embodiments, a pair of opposing cantilevered tables may share a common drive platform configured for transporting the scanner component between tables. In some embodiments, the drive platform may include a branched rail or track system configured to enabling transporting the scanner component between rows of pairs of opposing cantilevered tables.

In further example embodiments, a pivot mechanism may be included for adjusting an orientation of the CT scanner. Thus, the scanner component may be advantageously configurable for multiple scanning modes including a horizontal scanning mode and a vertical scanning mode. In some embodiments, the drive platform may be a curved drive platform. In further embodiments, the cantilevered table may include a tension support for a cantilevered end thereof In yet further example embodiments, a vertical low-cost CT system is provided comprising a vertically extending drive platform and a scanner component defining a center opening configured for receiving a portion of a patient's anatomy, wherein the scanner component is movably mounted relative to the drive platform whereby the scanner component may be controllably vertically translated along the drive platform so as to translate the scanner component relative to a patient.

BRIEF DESCRIPTION OF THE DRAWINGS

The present disclosure is further described in the detailed description which follows, in reference to the noted plurality of drawings by way of non-limiting examples of embodiments of the present disclosure.

DETAILED DESCRIPTION

New and improved CT imaging systems are presented herein which are low cost, fully self-contained and easily installed/used.

In example embodiments, one improvement includes the elimination of the cantilevered telescoping table used in typical CT systems. Rather, than employ this complex table design which is moved relative to a stationary CT scanner, in accordance with various embodiments disclosed herein, CT systems are provided which implement an integrated and self-contained drive system for moving a CT scanner component relative to a fixed or static platform/base which also functions as a low cost patient support. This design change advantageously enables the CT system to fit into a smaller room, e.g., into standard 10×10 ft (3×3 meter) rooms or smaller.

In further example embodiments, the CT systems presented herein are powered by an inexpensive battery system that can connect to almost any power the facility has, no matter how poor quality. The battery and power regulator controls advantageously enable the necessary power regularity.

In further example embodiments, the scanner is designed with a plurality of easily replaceable modules and remote diagnostics making it much easier to repair. Furthermore, scan options may be highly limited to the user, allowing very easy operation for the majority of scans that these types of institutions will need and are presently lacking. Separate modules may include, 1) an x-ray source module , e.g., including an x-ray source, collimator, transmission lenses/optics, filters, etc., 2) a detection module, e.g., including a detection array, receiving lenses/optics, filters such as scatter filters, etc. 3) one or more control modules, e.g., including scanner position controls, data processing components, network integration components, etc. and 4) a power module, e.g., including a battery, converters, power regulators, surge protectors, etc.).

In further example embodiments, the CT systems presented herein may combine a self-contained drive system for moving a CT scanner component relative to a fixed or static platform/base with a movable table. In some embodiments, the movable table may include one or more hinged segments for allowing reconfiguring and/or collapsing of portions of the table, e.g., so as to reduce an overall footprint and save space. In further example embodiments a vertical position of the CT scanner relative to the table may be adjustable, e.g., via the self-contained drive system.

In further example embodiments, the CT systems presented herein may include an integrated patient alignment mechanism (such as an alignment head board directly) which is directly connected to the CT system. In particular the alignment mechanism may be secured relative to a housing of the scanning component and/or a base of the CT system. The use of an integrated patient alignment mechanism that is secured relative to the CT system improves the adaptability of the system to scanning different anatomical regions while maintaining proper alignment and thus ensures greater reliability and improves the ease of use of the CT system by negating the need to manually align the system relative to a patient. In further example embodiments, the integrated alignment mechanism may advantageously include a one or more patient alignment features for guiding positioning of a patient, e.g., of a particular portion of a patient's anatomy, relative to the alignment mechanism. For example, the patient guide features may include markings, projections, grooves or other patient alignment features for positioning and orientating a patient relative to the alignment mechanism. The integrated alignment mechanism may further include one or more patient fasteners for securing a patient, e.g., a particular portion of a patient's anatomy in a particular position/orientation relative to the alignment mechanism. Thus, for example, in some embodiments, the integrated alignment mechanism may include one or more straps, ties, belts, clips or other patient fasteners.

Advantageously, the integrated patient alignment mechanism may be configured for a particular portion of the patient's anatomy. For example, in some embodiments, the patient alignment mechanism may include a headboard secured relative the system and adapted to facilitate proper alignment of a patient's head. In other embodiments, the patient alignment mechanism may include an arm rest for positioning and securing an arm relative to the CT system. In some embodiments, the patient alignment mechanism may be interchangeable, e.g., in order to enable selection of the appropriate alignment mechanism for a particular portion of the patient's anatomy. In further example embodiments, the patient alignment mechanism may define a plurality of different alignment configurations for the same portion of the patient's anatomy. These different alignment configuration may, e.g., correspond to different scanning protocols/applications. In some embodiments, the patient alignment mechanism may enable controllably adjusting a position and/or orientation of a portion of the patient's anatomy, e.g., to a selected position/orientation. Notably, the CT system may be configured to register the selected configuration of the patient alignment mechanism with respect to the corresponding image data. In further example embodiments, scanning protocols/applications may be pre-registered for a particular alignment mechanism and/or configuration thereof. Thus, in some embodiments, confirmation of a particular alignment mechanism and/or configuration thereof may be required by the system prior to initiating a corresponding scanning protocol/application. In some embodiments, a scan sequence may be facilitated by automatically adjusting or otherwise guiding adjustment of patient orientation/alignment between scans. For example, in some embodiments, a scan sequence may involve automatically adjusting or otherwise prompting adjustment of a configuration of the alignment mechanism between scans. In other embodiments, a scan sequence may involve prompting swapping of a first alignment mechanism for a second alignment mechanism between scans.

In further example embodiments, a plurality of beds may be configured to share a single CT system. Thus, e.g., in some embodiments, the self-contained drive system may advantageously enable transporting the CT system between beds. For example, a set of rails may be used to selectively transport a CT system between two oppositely positioned cantilevered beds. In further embodiments, a branched rail or track system may be used to selectively transport a CT system between a rows of beds as well.

In example embodiments, the CT systems presented herein may utilize a pivot type mechanism for adjusting an orientation of the CT system. Thus, in some embodiments, a single CT system may include multiple modes for both horizontal and vertical scanning configurations. In further example embodiments, a low cost vertical scanner is presented for saving space and reducing an overall footprint of the machine.

Note that in some embodiments, a movable MRI scanner component may be utilized instead of the CT scanner component in constructing low-cost Mill machines. The low-cost MRI systems may include similar features and functionalities as described above with respect to the low-cost CT systems.

Figure 1:
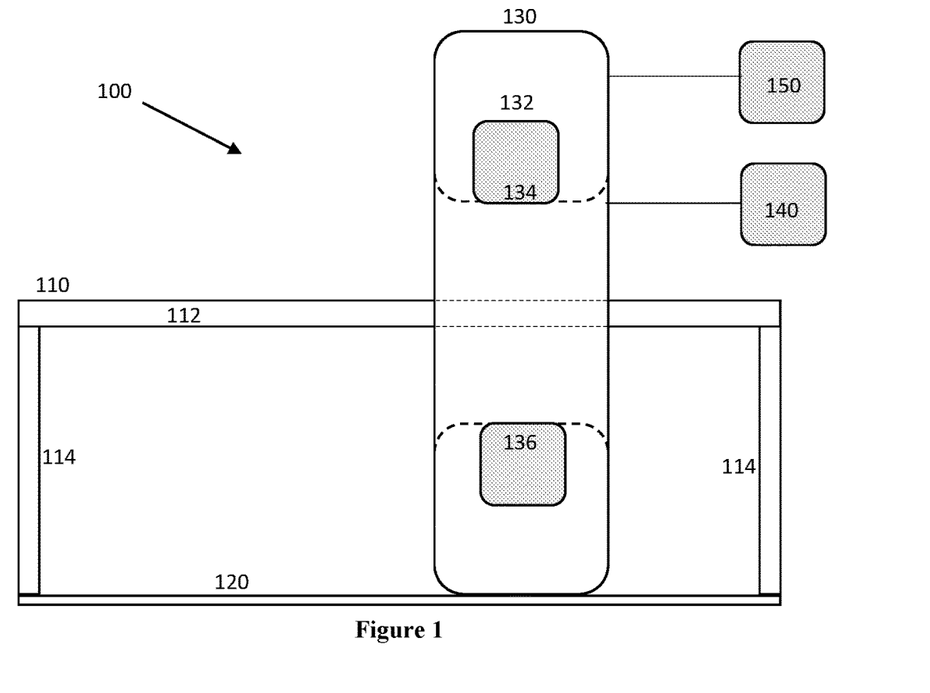
FIG. 1 depicts an exemplary low-cost CT system, according to embodiments of the present disclosure.

FIG. 1 depicts an exemplary low-cost CT system 100, according to embodiments of the present disclosure. The low-cost CT system 100 advantageously includes structural framework of a patient support table 110 including a patient support surface 112 extending between opposing support struts 114 spaced apart from one another. The struts 114 may include base portions thereof for mounting/anchoring the support table to a floor/ground. The patient support surface 112 may be a generally planar or flat surface and may preferably exhibit a high degree of radiolucency so as to not interfere with the CT scan. In example embodiments, the table 110 may be configured such that the support surface is substantially horizontal and parallel to the floor/ground. A drive platform 120 for the CT system 100, (e.g., a rail track) may also extend between the opposing support struts 114, for example, proximal to the base portions thereof. The drive platform 120 may be substantially parallel to the patient support surface. In some embodiments, the drive platform 120 may further act as a base of the table 110 providing improved structural stability and mounting stability to the table 110. A CT scanner 130 including a scanning component 132 defining a center opening (e.g., sized/shaped, for receiving a portion of a patient's anatomy) may be movably mounted relative to the drive platform 120 with the patient support surface 112 passing through the center opening. Thus, the CT scanner 130 may be controllably translated along the drive platform 120 so as to translate the CT scanner 120 relative to the patient support surface 112. The CT scanner 130 may be approximately 2 feet in length and less than 3 feet in length and the drive platform 120 and/or patient support surface 112 may be approximately 8 feet in length and less than 10 feet in length.

The system in FIG. 1 further includes a battery system 140 (which may be a modular component thereof) configured for regulating power to the CT system. In particular, the battery system 140 may act in conjunction with an uneven or unreliable external power source to normalize the power supply provided to the CT system. The battery system 140 may act like a Uninterruptible Power Supply (UPS) system and may be capable of suppling the necessary power for maximum x-ray exposure (e.g., 12 kwatt+), even where the wall power source is incapable of providing such power. In example embodiments, a power distribution unit (PDU) assembly may advantageously be configured to require a minimal external power supply connection prior to allowing for operation of the CT imaging system. Thus, e.g., while the CT imaging system may include the battery system 140 solely for supplementing an irregular power supply, e.g., from a wall connection, a wired power supply connection may be required prior to operation of the device. In other embodiments, if external power falls below a certain quality threshold, it may supplemented or replaced by battery power.

The system of FIG. 1 may further include other modular components such as an x-ray source module 134, e.g., including an x-ray source, collimator, transmission lenses/optics, filters, etc., 2) a detection module 136, e.g., including a detection array, receiving lenses/optics, filters such as scatter filters, etc. 3) and one or more control modules 150.

Figure 2:
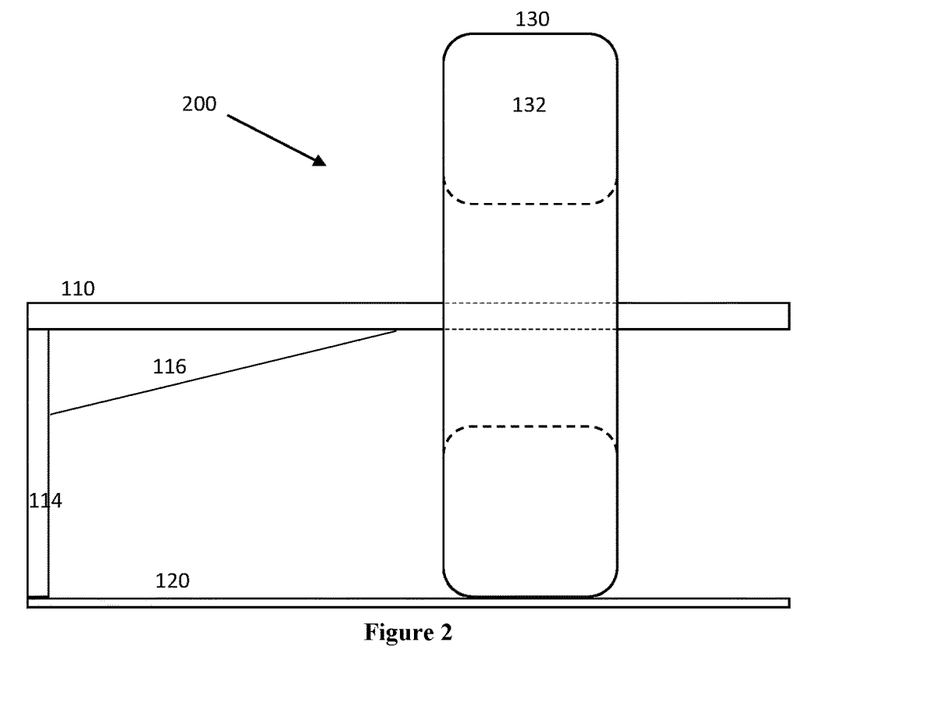
FIG. 2 depicts a variation on the low-cost system of FIG. 1 where a patient support surface of a table is cantilevered, according to embodiments of the present disclosure.

FIG. 2 depicts a variation 200 on the low-cost CT system 100 of FIG. 1, where the patient support surface 112 of the table 110 is cantilevered. In the depicted embodiment, the table 110 of variation 200 further includes a truss support 116 for supporting the cantilevered configuration of the patient support surface may enable extending a scannable region of the patient support surface to the ends thereof. Notably the truss support 116 may be dimensioned so as to not interfere with a full translational range of motion of the CT scanner. Since translation of the CT scanner 130 is only limited by one side of the table 110 (i.e. by the single support by a strut 114), the variation 200 is able to extend a scannable region of the cantilevered end of the patient support surface to a terminus thereof. This can be contrasted with the embodiment of FIG. 1, where translational motion of the CT scanner 130 is bounded by the struts 114, thereby limiting a scannable region of the patient support surface 112 of the table 110 in FIG. 1 relative to that in FIG. 2.

Figure 3A:
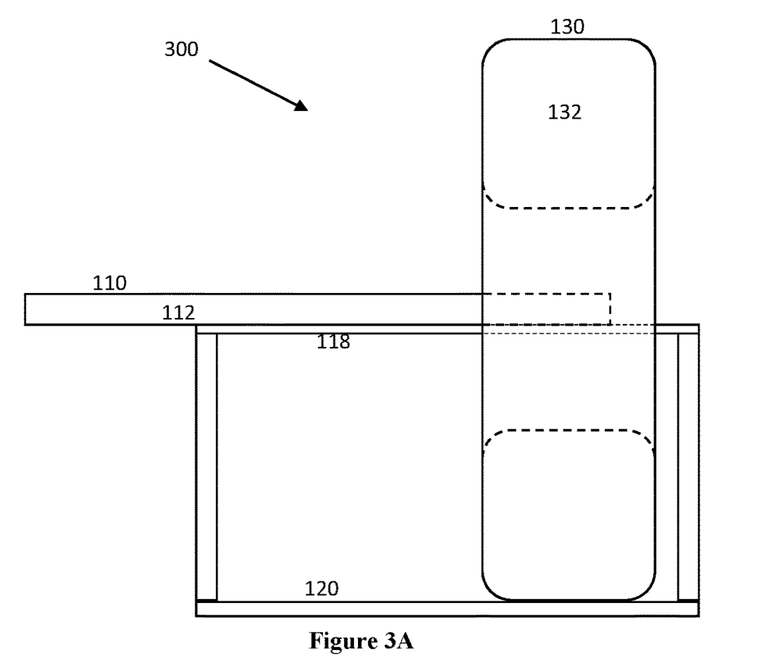
FIGS. 3A-3F depicts variations of the low-cost CT system of FIG. 1 combining the advantages of a drive platform with a table including a translatable patient support surface, according to embodiments of the present disclosure.
Figure 3B:
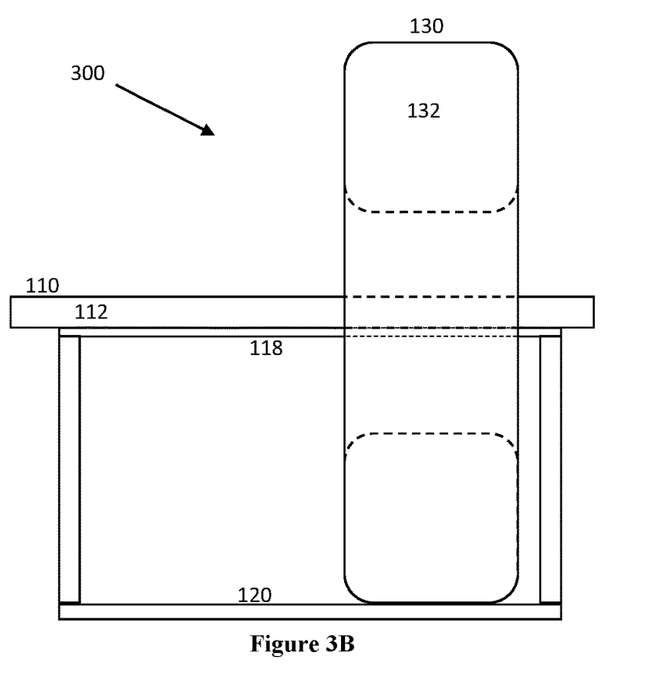
Figure 3C:
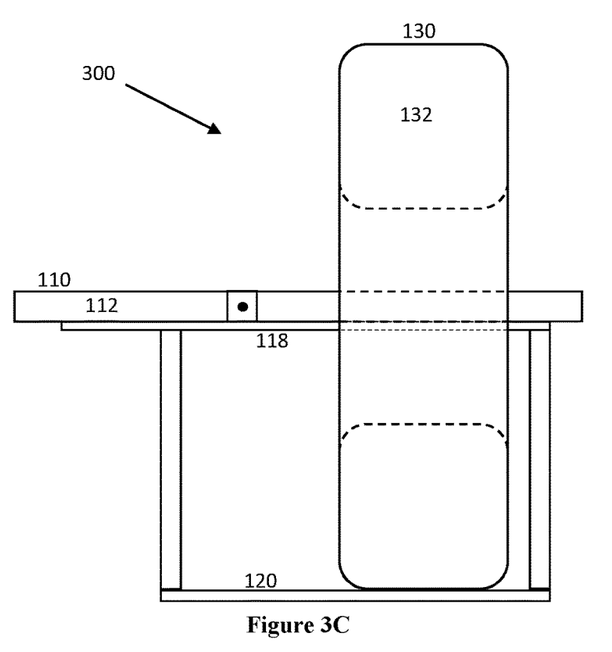
Figure 3D:
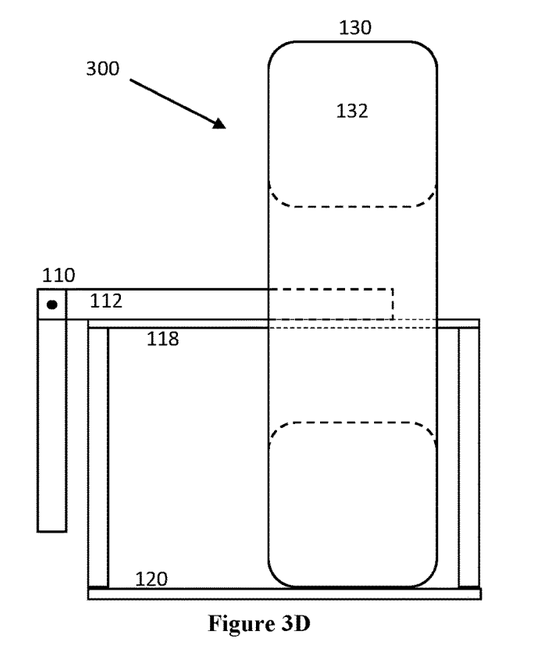
Figure 3E:
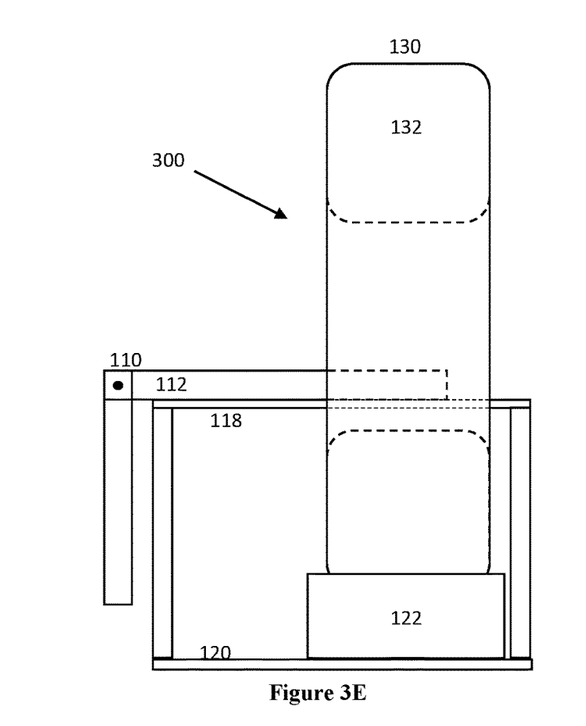
Figure 3F:
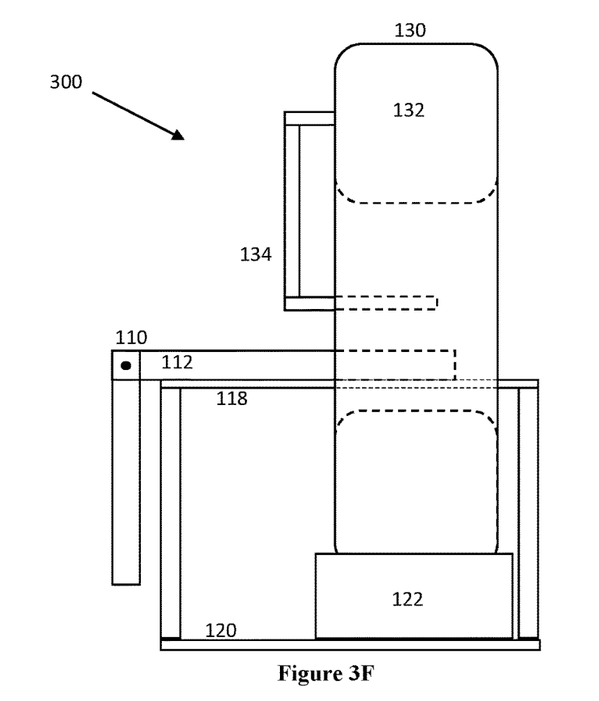

FIGS. 3A-3F depict a further variations 300 of the low-cost CT system 100 of FIG. 1. In particular, variations 300 combine the advantages of a drive platform 120 with a table 110 including a translatable patient support surface 112. Advantageously the translatable patient support surface 112 extends a scannable region of the patient support surface to the terminal ends thereof thereby enabling reducing the size (e.g., length) of the table 110 of FIGS. 3A-3F relative to the size of the table 110 in FIG. 1. Translation of the patient support surface may be enabled by a support surface drive platform 118 (e.g., a rail track). FIG. 3A depicts the patient support surface having been translated laterally so as to enable scanning of a terminal region thereof while FIG. 3B depicts the patient support surface 112 having been translated medially so as to reduce an overall footprint of the CT system variation 300. FIGS. 3C and 3D illustrate that in example embodiments, the CT systems disclosed herein may advantageously reduce a footprint of the table 110 by including one or more hinged/collapsible regions thereof. FIG. 3C depicts the table 110 in an un-collapsed state while FIG. 3D depicts the table 110 in a collapsed state. Notably, combinations of multiple hinged/collapsible regions may be preferable so as to maximize the configurability of the table 110. FIG. 3E illustrates that in example embodiments, the CT systems disclosed herein may advantageously include an alignment platform 122 for adjusting a horizontal and/or vertical position of the CT scanner 130 relative to the drive platform 120 and the table. Thus, e.g., in some embodiments, such as depicted in FIG. 3E, the scanner 130 may be translated up so as to allow for better patient alignment of a particular anatomical region. FIG. 3F illustrates that in example embodiments, the CT systems disclosed herein may be configured to include an alignment mechanism 134 for facilitation alignment of a patient's anatomical region relative to the CT scanner. Thus, in some embodiments, such as depicted in FIG. 3F, the alignment mechanism 134 may be securable relative to the scanner 130, e.g., relative to a scanning component 132 of the scanner 130. Advantageously aspects of including an alignment mechanism were described above.

Figure 4A:
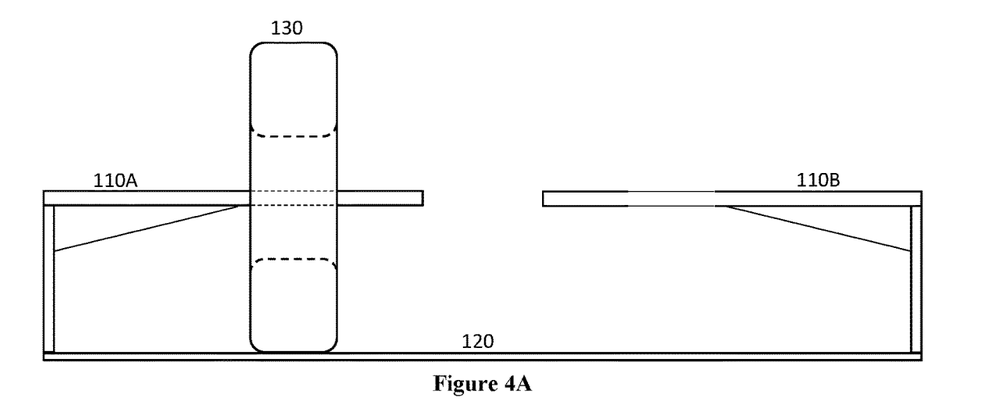
FIGS. 4A-4C depict variations of the low-cost CT system of FIG. 1 where a same CT scanner is shared between multiple patient tables, according to embodiments of the present disclosure.
Figure 4B:
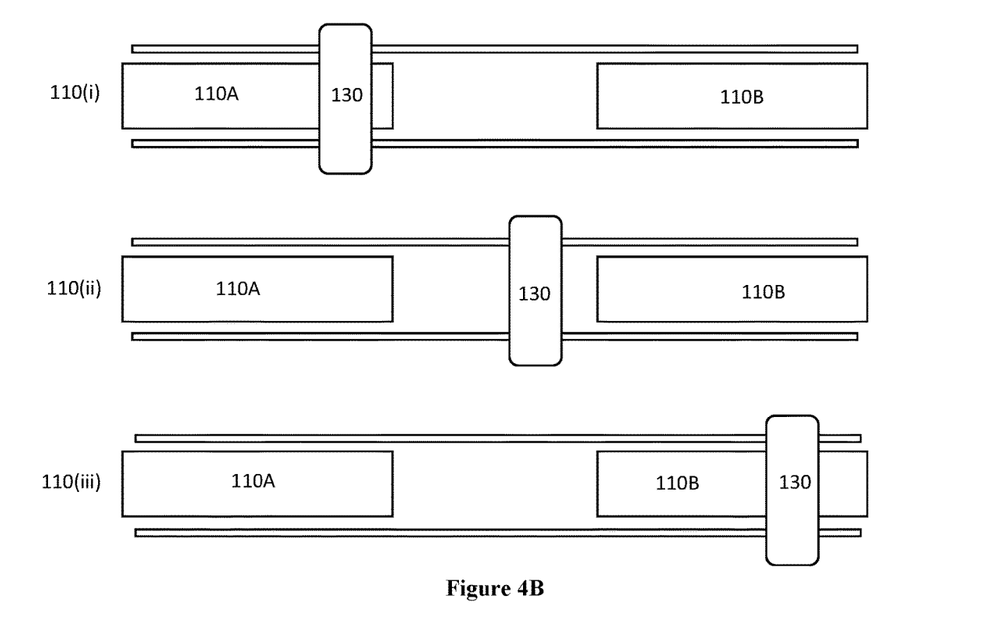
Figure 4C:
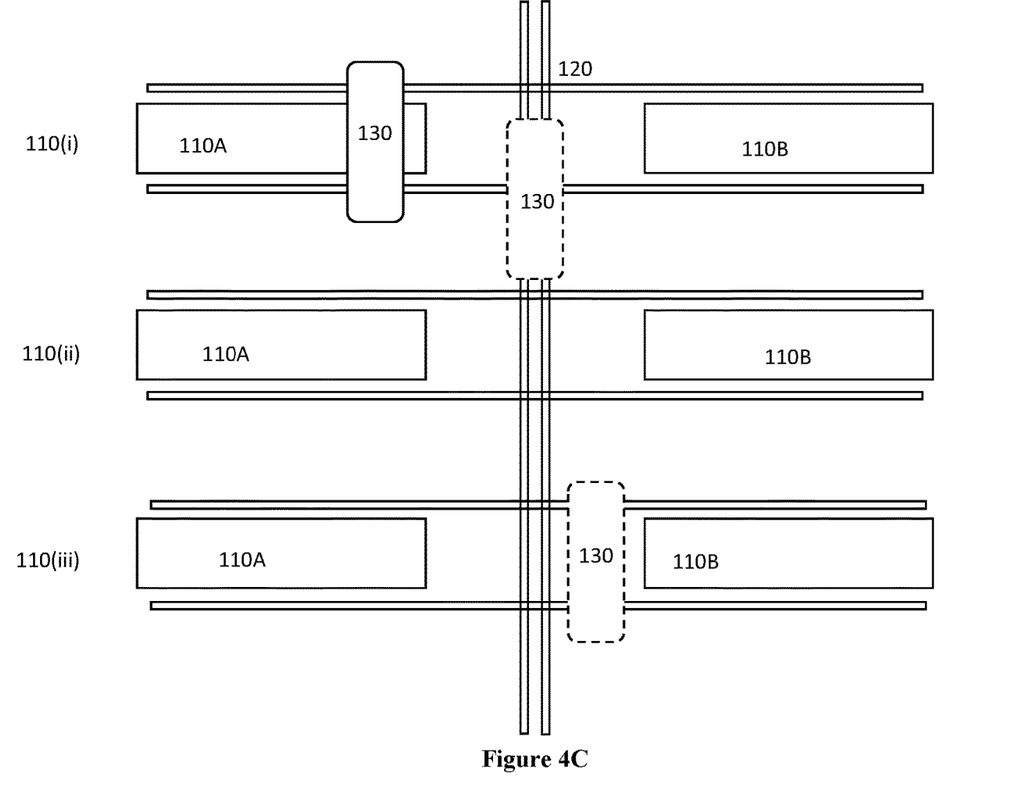

Referring now to FIGS. 4A-4B variations are depicted where a single CT scanner 130 is shared between multiple tables 110. For example, FIG. 4A depicts an implementation where oppositely positioned cantilevered tables 110A and 110B share a common drive platform 120 which enables transport of CT scanner 130 between the tables (inter-table transport). FIG. 4B depicts an overhead view where 3 table pairs 110(i) 110(ii) and 110(iii) (three rows of tables) are each configured similar to the table pair in FIG. 4A to share a common CT scanner. Notably, in some embodiments, a branched rail or track system 120 may be used to selectively transport a single CT system 130 between a rows of beds as well. For example, as depicted in FIG. 4C a single CT system 130 may be translated from a first table pair 110(i) to a third table pair 110(ii) via a branched rail or track system 120. Thus, e.g., an entire wing may be configured to share a same CT system 30 so as to not monopolize the space.

Figure 5:
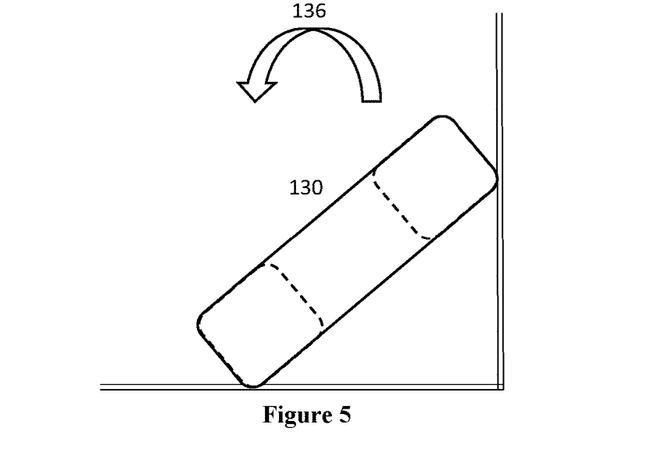
FIG. 5 illustrates a scanner with a pivot type mechanism for adjusting an orientation of the scanner, according to embodiments of the present disclosure, according to embodiments of the present disclosure.
Figure 6A:
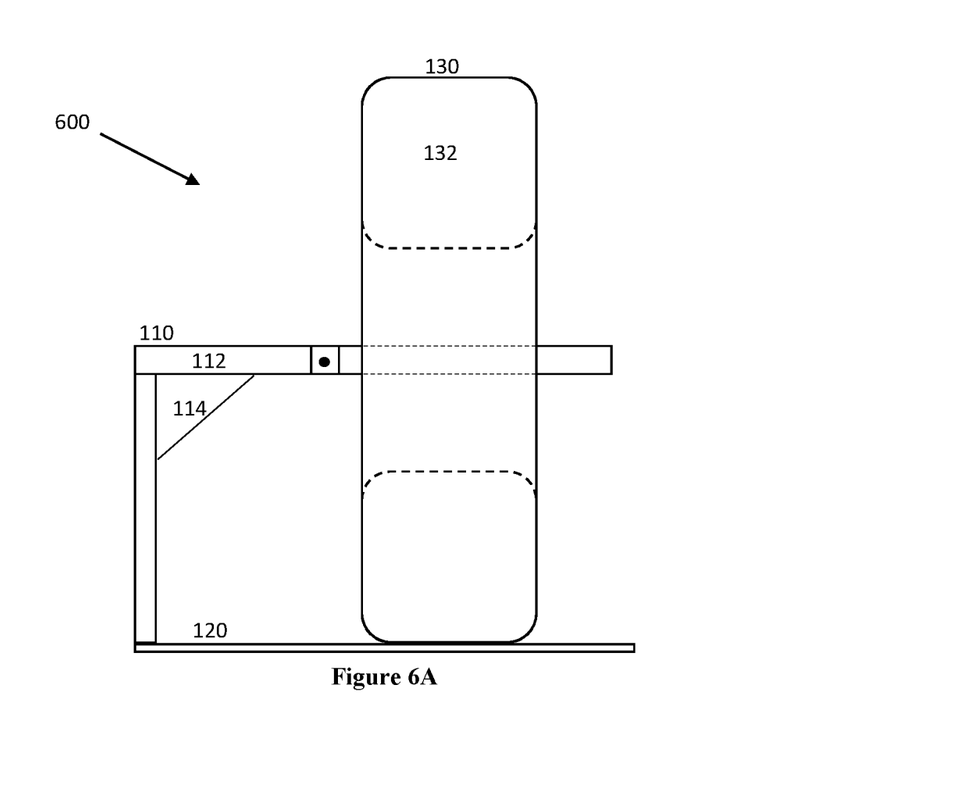
FIGS. 6A-6C and FIG. 7 illustrate variations where a single CT system includes multiple modes for both horizontal and vertical scanning configurations, according to embodiments of the present disclosure.
Figure 6B:
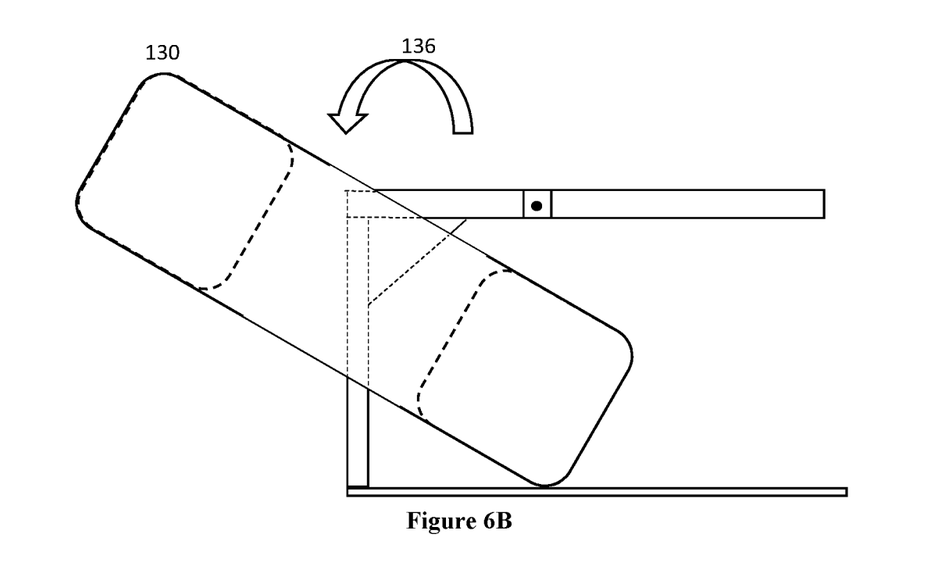
Figure 6C:
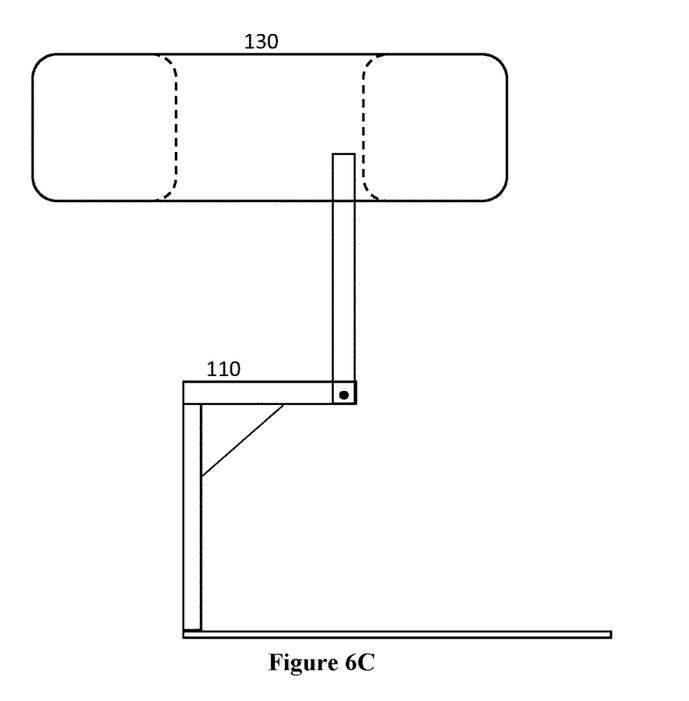
Figure 7:
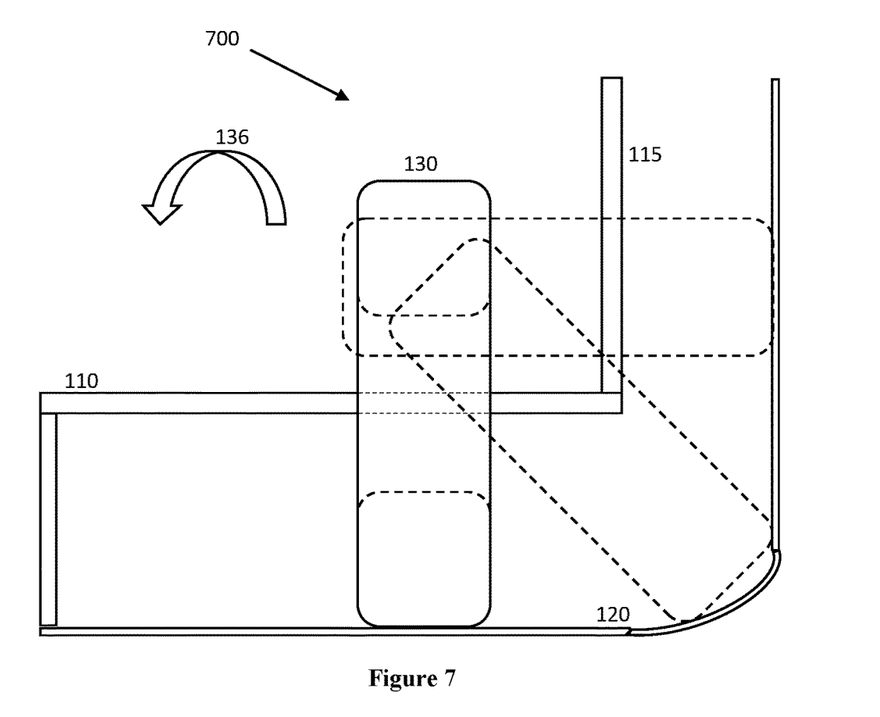
Figure 8:
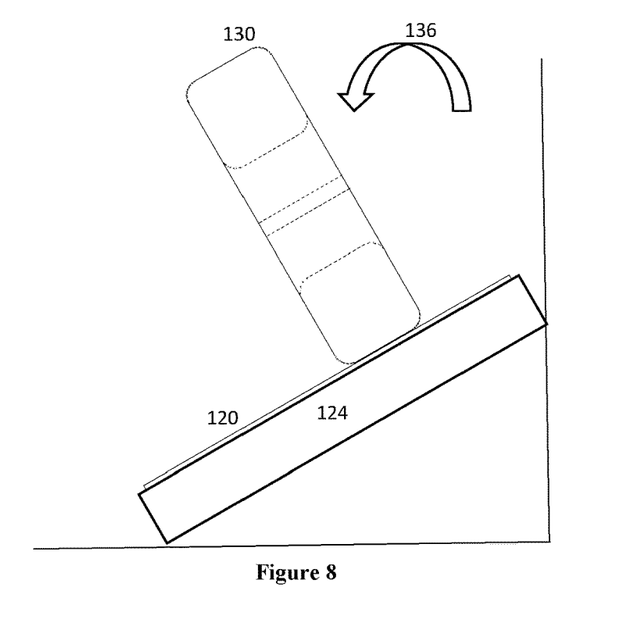
FIG. 8 illustrates how in some embodiments pivoting an orientation of the scanner may include pivoting a drive platform including a base support structure thereof, according to embodiments of the present disclosure.

FIG. 5 illustrates the principle that in example embodiments the CT scanner 130 may utilize a pivot type mechanism 136 for adjusting an orientation of the CT scanner 130. Thus, in some embodiments, a single CT system may include multiple modes for both horizontal and vertical scanning configurations. FIGS. 6A-C illustrate one such variation 600. In particular, in FIG. 6A a scanner 130 starts in a horizontal scanning position. In FIG. 6B the scanner is pivoted, e.g., using pivot mechanism 136, resulting in the scanner 130 being reconfigured to a vertical scanning position (FIG. 6C). Note that in the depicted embodiment, a hinged segment of the cantilevered table 110 is also pivoted resulting in transforming the table 110 into a chair-type structure. Notably, a vertical scanning position may advantageously reduce a footprint of the system, which may be advantageously from a space utilization standpoint. For example, where space for a horizontal type scan isn't currently available a vertical scan may be used in the meantime. FIG. 7 illustrates a further example embodiment of a variation 700 where a single CT system 130 includes multiple modes for both horizontal and vertical scanning configurations. In particular, FIG. 7 illustrates utilizing a curved drive platform 120 to pivot the CT system 130 from a horizontal scan configuration to a vertical scan configuration. Also notable is the fact that the table 110 illustrated in FIG. 7, while still cantilevered, includes a tension support 115 (e.g., from the ceiling) for the cantilevered end thereof. This provides greater table support and stability while still providing clearance for transitioning between vertical and horizontal scan modes. With reference now to FIG. 8 is noted that in some embodiments, pivoting the CT system may also include pivoting a drive platform 120 which may include pivoting a base support structure 124.

Figure 9:
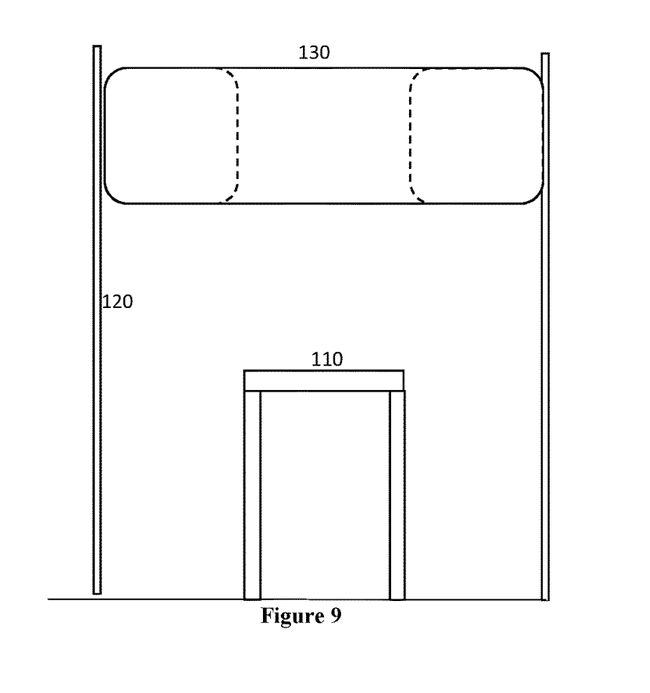
FIG. 9 depicts a low cost vertical scanning system, according to embodiments of the present disclosure.

In further example embodiments, such as depicted in FIG. 9, a low cost vertical scanning system 900 is presented. In particular the scanner 130 may have a fixed orientation that provides for vertical scanning. A patient support 110 may also be provided. In some embodiments (not depicted), the drive platform 120 for the scanner 130 may include 2 or more rails evenly distributed around a perimeter of the scanner 130 thus providing for increased support of the scanner 130.

Advantageously, in some embodiments, the new and improved CT imaging systems presented herein include modular type designs which facilitate maintenance/adaptability thereof. For example, as noted above, a same scanner component and internal drive system may be utilized in conjunction with different bases/platforms depending on the particular application, Thus, in some embodiments, the CT scanning component and internal drive system may be configured to enable mounting thereof relative to a plurality of different types of bases/platforms. In this way a hospital may easily refit a single machine for different purposes. Similarly, in some embodiments, the bases/platforms presented herein may be adapted to enable mounting different types of imaging modalities, such CT, x-ray, ultrasound etc. This adaptable/interchangeable modular type design also increases manufacturing efficiencies in producing the individual components.

Notably, the modular design approach disclosed herein extends with respect to functional sub-systems of the CT systems presented herein. For example, the x-ray source sub-system and detection sub-system may be modular components of the scanner component. Similarly, the control sub-system and/or power sub-system may be modular components of the base/platform component. Thus, in example embodiments, repair of a damaged sub-system may be facilitated by simply swapping out the entire modular sub-system for a new working sub-system. In this way the CT system may continue to function while the replaced damaged sub-system is repaired. Thus, in example embodiments a modular design may include 1) a modular x-ray source sub-system, e.g., including an x-ray source, collimator, transmission lenses/optics, filters, etc., 2) a modular detection sub-system, e.g., including a detection array, receiving lenses/optics, filters such as scatter filters, etc. 3) a modular control sub-system, e.g., including scanner position controls, data processing components, network integration components, etc. and 4) a modular power sub-system, e.g., including a battery, converters, power regulators, surge protectors, etc.) While exemplary embodiments envision a four subsystem modular component design it should be appreciated that other modular configurations may be employed. For example, in some embodiments, the control sub-system may include several distinct interchangeable modular components.

In example embodiments, the scan user interface may be greatly simplified for example, limited to present protocols (e.g., one or two preset protocols). A simple interface to scan and communicate and transfer data to a HIS/RIS/PACS system may be included (e.g., in Siemens Syngo format). Moreover the system may be manufacture utilizing pre-existing components such as DAS, Detector, X-ray tube, HVPS, workstation software, recon software, and portable base. In a mobile ambulatory stetting, the CT system may be directly integrated/packaged with a vehicle, a telemedicine system and/or other medical equipment.

In further example embodiments, the CT systems presented herein may include a nested, e.g., a telescopic scanner component configuration. In a nested configuration a first housing of the CT scanner component may be advantageously nested within a second housing of the CT scanner component. In some embodiments, the second housing may include an inner diameter substantially equal to the outer diameter of the first housing. Moreover, in some embodiments, the second housing may have a greater length than the first housing. Thus, in some embodiments a first ring-shaped housing member may be positioned within a second ring-shaped housing, e.g., proximal to a first open end thereof In general, the first and second housings may be shaped as nested right circular hollow cylinders. In some embodiments, the first and second housings may be nested like Russian nesting dolls with the second housing fitting within a center cavity defined by the first housing. In alternative embodiments, the first and second housings may be nested with the first housing fitting into a ring-shaped slot defined by second housing, e.g., between outer and inner diameters thereof. Advantageously, in some embodiments, the first and second housings may cooperate to define a cavity space (e.g., with the first housing and the second housing forming front and back covers encapsulating the cavity space). This cavity space may be expanded or collapsed by moving the first and second covers relative to one another. Advantageously, the first housing may define an inner opening configured. e.g., sized/shaped, for receiving a portion of a patient's anatomy (such as the patient's head) while the second housing may define a wider opening configured for receiving a greater portion of a patient's anatomy (such as a patients head neck and shoulders). In some embodiments, the outer housing may advantageously act as a radiation shield, e.g., to help contain radiation from the scanner component and mitigate radiation scatter. In further embodiments, the first housing may be stationary or fixed relative to the second housing. Thus, in some embodiments, the first housing may include an internal translation drive for translating a rotatable disk/drum housed therein (e.g., thereby translating a beam bath relative to a patient). In other embodiments, the first housing may be configured to translate relative to the second housing. In some embodiments, this may be for storage/alignment purposes, e.g., for enabling collapsing the first housing into the second housing so as to reduce a size footprint of the CT scanner component when the scanner component isn't in use, so as to enable positioning of the scanner relative a portion of a patient's anatomy to be scanned and/or so as to enable positioning the first and our second housing in a position to provide optimal radiation shielding for a particular scan position. In some embodiments, the second housing may be configured to telescopically extend relative to the first housing, e.g., prior to initiating a scan. In further embodiments, the first housing may be configured to translate relative to the second housing so as to implement a scan (e.g., so as to translate a beam path relative to the patient). Thus, in some embodiments, the first and/or second housing may be positioned relative to the patient so as to align the CT scanner component with the patient. The first and/or second housings may also be positioned relative to each other to provide optimal radiation protection or to expand an inner cavity space for allowing for internal translation of scanner components. A scan may then be initiated by translating the first housing relative to the second housing (e.g., so as to translate a beam path relative to the patient). Notably, to provide optimal radiation shielding the CT scanner component may be configured such that the beam path is maintained in a central positioning relative to the first and/or second housing(s). This may advantageously minimize radiation scatter and unwanted exposure by the patient and/or a care provider.

Whereas many alterations and modifications of the disclosure will no doubt become apparent to a person of ordinary skill in the art after having read the foregoing description, it is to be understood that the particular embodiments shown and described by way of illustration are in no way intended to be considered limiting. Further, the subject matter has been described with reference to particular embodiments, but variations within the spirit and scope of the disclosure will occur to those skilled in the art. It is noted that the foregoing examples have been provided merely for the purpose of explanation and are in no way to be construed as limiting of the present disclosure.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims.

The invention claimed is:

1. A low-cost CT system comprising:
a patient support table including a patient support surface extending between opposing support struts spaced apart from one another wherein the table further includes at least one hinged region of the patient support surface adapted for reconfiguring the patient support surface to reduce a footprint of the CT system;
a drive platform extending between the opposing support struts; and
a scanner component defining a center opening configured for receiving a portion of a patient's anatomy, wherein the scanner component is movably mounted relative to the drive platform with the patient support surface passing through the center opening whereby the scanner component may be controllably translated along the drive platform so as to translate the scanner component relative to the patient support surface.

2. The system of claim 1, wherein the struts include base portions thereof for mounting or anchoring the support table to a mounting surface.

3. The system of claim 2, wherein the drive platform extends between the base portions of the opposing support struts.

4. The system of claim 1, wherein the patient support surface is a planar surface.

5. The system of claim 4, wherein the drive platform is substantially parallel to the patient support surface.

6. The system of claim 4, wherein the support surface is substantially horizontal.

7. The system of claim 1, wherein the patient support surface exhibits a high degree of radiolucency so as to not interfere with imaging.

8. The system of claim 1, wherein the drive platform is a rail track.

9. The system of claim 1, wherein the drive platform also forms a base of the table providing improved structural stability and mounting stability to the table.

10. The system of claim 1, wherein the scanner component is less than 3 feet in length.

11. The system of claim 1, wherein the scanner component is approximately 2 feet in length.

12. The system of claim 1, wherein the drive platform is less than 10 feet in length.

13. The system of claim 1, wherein the drive platform is approximately 8 feet in length.

14. The system of claim 1, wherein the scanner component exhibits a low rotation speed of less than 1 rotation per second.

15. The system of claim 1, wherein the scanner component exhibits a low rotation speed of less than ½ a rotation per second.

16. The system of claim 1, wherein the scanner component includes a fixed collimator.

17. The system of claim 1, wherein different slice widths are achieved via a plurality of detector rows.

18. The system of claim 1, wherein the patient support surface of the table is laterally translatable relative to the struts of the table.

19. The system of claim 18, further comprising a support surface drive platform for enabling lateral translation of the patient support surface of the table.

20. The system of claim 18, wherein the lateral translation of the patient support surface extends a scannable region thereof to a terminal end thereof.

21. The system of claim 1, further comprising an alignment platform for adjusting a horizontal and/or vertical position of the scanner component relative to the drive platform and the table.

22. The system of claim 1, further comprising an alignment mechanism securable relative to the scanner component for facilitating alignment of an anatomical region of a patient.

23. A low-cost CT system comprising:
a patient support table including a cantilevered patient support surface;
a drive platform extending underneath the cantilevered patient support surface; and
a scanner component defining a center opening configured for receiving a portion of a patient's anatomy, wherein the scanner component is movably mounted relative to the drive platform with the patient support surface passing through the center opening whereby the scanner component may be controllably translated along the drive platform so as to translate the scanner component relative to the patient support surface and wherein the scanner component is shared between multiple tables.

24. The system of claim 23, wherein the table further includes a truss support.

25. The system of claim 23, wherein translation of the scanner component via the drive platform is not limited at the cantilevered end of the table thereby extending a scannable region of the cantilevered end to a terminus of the patient support surface.

26. The system of claim 23, wherein a pair of opposing cantilevered tables shares a common drive platform configured for transporting the scanner component between tables.

27. The system of claim 23, wherein the drive platform includes a branched rail or track system configured to enabling transporting the scanner component between rows of pairs of opposing cantilevered tables.

28. A low-cost CT system comprising:
a patient support table including a cantilevered patient support surface;
a drive platform extending underneath the cantilevered patient support surface;
a scanner component defining a center opening configured for receiving a portion of a patient's anatomy, wherein the scanner component is movably mounted relative to the drive platform with the patient support surface passing through the center opening whereby the scanner component may be controllably translated along the drive platform to translate the scanner component relative to the patient support surface and wherein the scanner component is configurable for multiple scanning modes including horizontal and vertical scanning modes; and a pivot mechanism for adjusting an orientation of the CT system.

29. The system of claim 28, wherein the drive platform is a curved drive platform.

30. The system of claim 28 wherein the cantilevered table includes a tension support for a cantilevered end thereof.

* * * * *